(12) United States Patent
Paris et al.

(10) Patent No.: US 7,749,987 B2
(45) Date of Patent: *Jul. 6, 2010

(54) CONTRACEPTION METHOD

(75) Inventors: Jacques Paris, Nice (FR); Jean-Louis Thomas, Charenton-le-Pont (FR); Michel Lanquetin, La Trinite (FR); Anny Lanquetin, legal representative, Laghet-La Trinite (FR); Jean-Philippe Lanquetin, legal representative, Belfort (FR)

(73) Assignee: Laboratorie Theramek (MC)

( * ) Notice: Subject to any disclaimer, the term of this patent is extended or adjusted under 35 U.S.C. 154(b) by 64 days.

This patent is subject to a terminal disclaimer.

(21) Appl. No.: 11/649,672

(22) Filed: Jan. 3, 2007

(65) Prior Publication Data

US 2007/0281912 A1    Dec. 6, 2007

Related U.S. Application Data

(63) Continuation-in-part of application No. 10/753,073, filed on Jan. 8, 2004, now abandoned, which is a continuation-in-part of application No. 09/284,147, filed as application No. PCT/FR97/01792 on Oct. 8, 1997, now Pat. No. 6,831,073, which is a continuation-in-part of application No. 09/423,108, filed on Oct. 29, 1999, now Pat. No. 6,906,049.

(30) Foreign Application Priority Data

Oct. 8, 1996  (FR) .................................. 96 12239
Oct. 25, 1999 (WO) ...................... PCT/FR99/02587

(51) Int. Cl.
*A61K 31/56* (2006.01)
*A61K 31/565* (2006.01)
*A61K 31/57* (2006.01)
*C07J 1/00* (2006.01)
*C07J 5/00* (2006.01)

(52) U.S. Cl. ...................... 514/169; 514/170; 514/171; 514/177; 514/178; 514/182; 552/595; 552/625; 424/811

(58) Field of Classification Search .................. 514/169, 514/170, 171, 177, 178, 182; 552/595, 625; 424/811

See application file for complete search history.

(56) References Cited

U.S. PATENT DOCUMENTS

| 3,271,392 | A | * | 9/1966 | Lefebvre | ...................... 540/94 |
| 4,628,051 | A | | 12/1986 | Pasquale | |
| 4,820,831 | A | | 4/1989 | Ogata | |
| 4,826,831 | A | | 5/1989 | Plunkett | |
| 5,108,995 | A | | 4/1992 | Casper | |
| 5,208,225 | A | | 5/1993 | Boissonneault | |
| 5,256,421 | A | | 10/1993 | Casper | |
| 5,382,573 | A | | 1/1995 | Casper | |
| 5,552,394 | A | | 9/1996 | Hodgen | ...................... 514/178 |
| 5,565,443 | A | | 10/1996 | Lanquetin | |
| 5,583,129 | A | | 12/1996 | Spona | |
| 5,585,370 | A | | 12/1996 | Casper | |
| 5,843,934 | A | | 12/1998 | Simpkins | ...................... 514/182 |
| 5,888,543 | A | | 3/1999 | Gast | ........................... 424/464 |
| 5,891,867 | A | | 4/1999 | Lanquetin | |
| RE36,247 | E | | 7/1999 | Plunkett et al. | ............. 514/170 |
| 6,500,814 | B1 | | 12/2002 | Hesch | |
| 6,831,073 | B1 | | 12/2004 | Lanquetin et al. | |
| 6,906,049 | B1 | | 6/2005 | Paris | |
| 6,995,149 | B1 | | 2/2006 | Endrikat | |
| 2004/0220163 | A1 | | 11/2004 | Paris | |

FOREIGN PATENT DOCUMENTS

| CA | 1332227 | 10/1994 |
| DE | 3229612 A1 | 2/1983 |
| EP | 0136011 | 4/1985 |
| EP | 0235090 | 9/1987 |
| EP | 0253607 | 1/1988 |
| EP | 0309263 | 3/1989 |
| EP | 0491415 | 6/1992 |
| EP | 0491438 | 6/1992 |
| EP | 0 770 388 A1 | 5/1997 |
| EP | 0911029 A2 | 4/1999 |
| EP | 1227814 | 8/2002 |
| FR | 2754179 | 4/1998 |
| GB | 2 216 420 | 10/1989 |
| WO | WO 90/04330 | 5/1990 |
| WO | WO 95/17194 | 6/1995 |
| WO | WO 96/09826 | 4/1996 |
| WO | WO 96/10991 | 4/1996 |

(Continued)

OTHER PUBLICATIONS

Bazin, et al. (1987) Br. J. Obstet. Gynecol., 94(12): 1199-1204.
Conard, et al. (1995) "Cardiovascular Risk Factors and Combined Estrogen-Progestin Replacement Therapy: A Placebo-Controlled Study With Nomegestrol Acetate and Estradiol,"0 Fertility and Sterility, 65(5): 957-962.
Cano, et al. (CA 115:150824, abstract of Maturitas (1991), 13(1), 35-42).
Blanc, et al. (1998:856197, SCISEARCH, abstract of Clinical Therapeutics, (1998), 20(5): 901-912.
Fraser, et al. (Medline, DN 89261206, abstract of Maturitas, (Mar. 1989), 11(1), 21-34).
Catherino, William et al. (1995) (DN 124:21954, HCAPLUS, abstract of J. Steroid Biochem. Mol. Biol., 55(2): 239-46.
Jamin (1992) Rev. fr. Gynecol. Obstet, 87(6): 370-376.
Paris, et al. (1983) Arzneimittelforschung, 35(5): 710-715.

(Continued)

*Primary Examiner*—Johann R Richter
*Assistant Examiner*—James H Alstrum Acevedo
(74) *Attorney, Agent, or Firm*—John P. White; Cooper & Dunham LLP

(57) ABSTRACT

A method of achieving contraception in a woman which comprises administering orally to said woman an estroprogestative composition comprising nomegestrol acetate and an estrogen is provided.

15 Claims, No Drawings

FOREIGN PATENT DOCUMENTS

| | | |
|---|---|---|
| WO | WO 97/04784 | 2/1997 |
| WO | WO 97/41868 | 11/1997 |
| WO | WO 97/41869 | 11/1997 |
| WO | WO 97/41870 | 11/1997 |
| WO | WO 97/41871 | 11/1997 |
| WO | WO 97/41872 | 11/1997 |
| WO | WO 98/04246 | 2/1998 |
| WO | WO 98/04265 | 2/1998 |
| WO | WO 98/04266 | 2/1998 |
| WO | WO 98/04267 | 2/1998 |
| WO | WO 98/04268 | 2/1998 |
| WO | WO9815279 | 4/1998 |
| WO | WO 98/35682 | 8/1998 |
| WO | WO 99/09993 | 3/1999 |
| WO | WO 99/09996 | 3/1999 |
| WO | WO 99/12531 | 3/1999 |
| WO | WO 99/13882 | 3/1999 |
| WO | WO 01/30358 | 5/2001 |
| WO | WO0130355 | 5/2001 |
| WO | WO 97/23228 | 7/2001 |

OTHER PUBLICATIONS

Powers, et al. (1985) Am. J. Obstet. Gynecol., 152(8): 1099-1106.
Reynolds, Martindale The Extra Pharmacopoeia, 30$^{th}$ Edition, 1993, Pharm. Press pp. 1166-1198.
Sitruk-Ware, R., "Pharmacology of Oral Contraceptives!" Rev. Pat., Dec. 1, 1995, 45(19): 2401-2406.
Affinito et al., (1998) "*Ultrasonographic Measurement Of Endometrial Thickness During Hormonal Replacement Therapy In Postmenopausal Women*". Ultrasound Obstet. Gynecol. 1998; 11: pp. 343-346.
Astedt, et al. (1977) "*The Natural Oestrogenic Hormone Oestradiol As A New Component Of Combined Oral Contraceptives,*" British Medical Journal, Jan. 29, 1997, p. 269.
Barrett-Connor et al., (1989) "*Estrogen Replacement And Coronary Heart Disease*" Cardiovascular clin., vol. 19, No. 3, pp. 159-172.
Basdevant et al., (Dec. 1991) "*Effects Of Nomegestrol Acetate (5 Mg/D), On Hormonal, Metabolic And Hemostatic Parameters In Premenopausal Women*" Contraception, vol. 44, No. 6 , pp. 599-605.
Bazin et al., (1989) "*Etude De La Physiologie Et De La Morphologie Folliculaires Après Administration D'acètate De Nomègestrol : Relation Effet-Dose*" 9ième Congrés français d'endocrinologie, Strasbourg, Oct. 12-14, 1989, including an English translation.
Bergink, et al., (1981) "*Effect Of Oestriol, Oestradiol Valerate And Ethinyloestradiol On Serum Proteins In Oestrogen-Deficient Women,*" Maturitas, 3 (3-4) : 241-247.
Bernard A. M. et al., (1994) "*Comparative Evaluation Of Two Percutaneous Estradiol Gels In Combination With Nomegestrol Acetate In Hormone Replacement Therapy*". XIV World Congress of Gynecology and Obstetrics, FIGO, Montreal, Sep. 24-30, 1994.
Bernard A. M. et al., (1994), *Menopausal: Bone and Therapeutic Regimens (Cont)*. International Journal of Gynecology & Obstetrics, pp. 124.
Birkauser M. et al., (1995) "*Substitution Hormonale: Une Indication Bien Posée Et Des Schémas De Traitement Individuels Sont Déterminants Pour Le Succès Du Traitement*" Med. et Hyg., 1995, 53: 1770-1773, including an English translation of the abstract.
Bocanera R et al., "*Effect Of A HRT Regime (Micronized 17-Estradiol And Medroxy Progesterone Acetate) On The Endometria And Bleeding Pattern Of Climacteric Women*" 7th International Congress on the Menopause, Stockholm, Jun. 20-24, 1993, abstr 40.
Bonnar, et al. (1987) "*Blood Coagulation With A Combination Pill Containing Gestodene And Ethinyl Estradiol,*" Int. J. Fertil., Suppl., pp. 21-28.
Bonnar, J. (1987) "*Coagulation Effects Of Oral Contraception*" Am. J. Obstet. Gynecol. vol. 157, pp. 1042-1048.
Botella et al. "*Regulation Of Rat Uterine Steroid Receptors By Nomegestrol Acetate, A New 19-Nor-Progesterone Derivative*" Abstract of J. Pharmacol. Exp. Ther. Feb. 1989; 248(2): 758-61.
Botella et al. "*Kinetic Analysis Of The Binding Of Nomegestrol Acetate To The Progesterone Receptors In Rat Utuerus By Competition Studies*" Fundam. Clin. Pharmacol. 1990; 4(5): 511-23.
Botella et al. "*Lack of Estrogenic Potential of Progesterone-Or 17-Norprogesterone-Derived Progestins As Opposed To Testosterone Or 19-Nortestosterone Derivatives On Endometrial Ishikawa Cells*" J. Steroid. Biochem. Mol. Biol. Oct. 1995; 55(1): 77-84.
Buckman, et al. (1980) "*Differential Lipemic and Proteinemic Response To Oral Ethinyl Estradiol And Parenteral Estradiol Cypionate,*" Metabolism, vol. 29, No. 9, pp. 803-805.
Burkman, R.T. (1997) "*The Estrogen Component Of Ocs: Cardiovascular Benefits And Risks*" Int. J. Fertil. Womens Med., Suppl. 1, pp. 145-157.
Carranza-Lira, "*Endometrial Changes According To Hormone Replacement Therapy Schedule*"—Menopause: The Journal of North American Menopause Society, 1998, vol. 5, No. 2, pp. 86-89.
Cohen et al. "*Traitement Des Femmes En Périménopause Par 5 Mg/J D'acétate De Nomégestrol, 20 Jours Par Cycle*" Contracept. Fertil. Sex. (1992)—vol. 20, No. 11, 1054-1057, including an English language abstract.
Couzinet et al. "*The Antigonadotropic Activity Of Progestins (19-Norprogesterone And 19-Norprogesterone Derivatives) Is Not Mediated Through The Androgen Receptor*" J. Clin. Endocrinol. Metab. Dec. 1996; 4218-4223.
Couzinet B., et al. (1999) "*The Antigonadotropic Activity Of A 19-Nor-Progesterone Derivative Is Exerted Both At The Hypothalamic And Pituitary Levels In Women,*" The Journal of Clinical Endocrinology & Metabolism, vol. 84, No. 11, pp. 4191-4196.
Crook D. et al. "*Oral Contraceptives And Metabolic Risk Markers For Coronary Heart Disease*" Int. J. Fertil. 1991; 36; suppl. 1: pp. 38-46, Abstract only.
Csemicsky, et al. (1996) "*The Pharmacodynamic Effects Of An Oral Contraceptive Containing 3 Mg Micronized 17Beta-Estradiol And 0.150 Mg Desogestrel For 21 Days, Followed By 0.030 Mg Desogestrel Only For 7 Days,*" Contraception, 54, pp. 333-338.
Daly, L. & Bonnar, J. (1990) "*Comparative Studies Of 30 Microgr. Ethinyl Estradiol Combined With Gestodene And Desogestrel On Blood Coagulation, Fibrinolysis, And Platelets*" Am. J. Obstet. Gynecol. vol. 163, No. 1, part.2, pp. 430-437.
Desreux et al. "*Effects Of A Progestogen On Normal Human Breast Epithelial Apoptosis On Vitro And In Vivo*" The Breast (2003), 12, 142-149.
Dorangeon et al. "*Effects Of Nomegestrol Acetate On Carbohydrate Metabolism*" Diabete & Metabolisme (paris) (1993), 19, 441.
Dorangeon et al. "*Short Term Effects On Lipids And Lipoproteins Of Two Progestogens Used In Postmenopausal Replacement Therapy*" European Journal of Clinical Research (1992), 3: 187-193.
Dorangeon et al. "*Traitement De L'endométriose Par L'acétate De Nomégestrol*" Gynécologie, 1993, 1, 3, 139-143, including an English language abstract.
Doren & Schneider, "*Long-Term Compliance Of Continuous Combined Estrogen And Progestogen Replacement In Postmenopausal Women*" 1996—Maturitas 25, Journal of the Climacteric & postmenopause, pp. 99-105.
Doren et al., "*The Impact Of Different HRT Regimens On Compliance*" 1996 Int. J. Fertil, 41 (10), pp. 29-39.
Doren et al., "*Uterine Perfusion And Endometrial Thickness In Postmenopausal Women On Long-Term Continuous Combined Estrogen And Progestogen Replacement*"—Ultrasound Obstet. Gynecol.9, 1997—pp. 113-119.
Drapier Faure E., "*Le Traitement De La Ménopause Évitant Les Règles Est-Il Possible? Est-Il Souhaitable?*" Gynécologie, 1992, 43, 4-5 pp. 271-280, including English language abstract.
Duc et al. "*Interaction Of [3H] Nomegestrol Acetate With Cytosolic Progesterone Receptors From The Rat Uterus*" Steroids, Jun. 1991; 56(6): 325-328.
Duc at al. "*Antiandrogenic Properties Of Nomegestrol Acetate*" Arzneim. Forsch. Drug/res. 1995, 45(1): 70-74.
Eiken and Kolthoff, "*Compliance With Long-Term Oral Hormonal Replacement Therapy*"—Maturitas 22, J. Clim.Postmenop., 1995 pp. 97-103.

Eiken et al., "*Effect Of 10 Years' Hormone Replacement Therapy On Bone Mineral Content In Postmenopausal Women*" 1996—Elsevier Sci.lnc. Bone, vol. 19, No. 5, Suppl. pp. 191S-193S.

Eiken et al., "*Effects On Bone Mass After Eight Years Of Hormonal Replacement Therapy*"—British Journal of Obstetrics and Gynecology Jun. 1997, vol. 104, pp. 702-707.

Ettinger et al., "*Comparison Of Continuation Of Postmenopausal Hormone Replacement Therapy: Transdermal Versus Oral Estrogen*" Menopause: the Journal of the North American Menopause Society,1998, vol. 5, No. 3, pp. 152-156.

Fitzgerald, C., et al. "*A Comparison Of The Effects Of Two Monophasic Low Dose Contraceptives On The Inhibition Of Ovulation*," Advances in Contraception, (1994) 10, pp. 5-18.

Foidart et al. "*Impact Of Percutaneous Oestradiol Gels In Postmenopausal Hormone Replacement Therapy On Clinical Symtoms And Endometrium*" British Journal of Obstetrics and Gynaecology Mar. 1997, vol. 104, 305-310.

Fox et al, "*Six Months Endometrial Histology Data On Continuous Estradiol Combined With 4 Different Dosages Of Continous Dydrogesterone In More Than 300 Postmenopausal Women*" 7th International Congress on the Menopause, Stockholm, Jun. 20-24, 1993, abstr 119.

Hargrove et al. "*Menopausal Hormone Replacement Therapy With Continuous Daily Oral Micronized Estradiol And Progesterone*", Obstet Gynecol, 1989, 73: 606-612.

Hart et al., "*Long-Term Effects Of Continuous Combined HRT On Bone Turnover And Lipid Metabolism In Postmenopausal Women*" -Osteopros Int., 1998, 8, pp. 326-332.

Hirvonen et al. (1998) "*New Natural Oestradiol/Cyproterone Acetate Oral Contraceptive For Pre-Menopausal Women*," Maturitas, 10(3), pp. 201-213.

Hirvonen et al. (1995) "*Oral Contraceptive Containing Natural Estradiol For Premenopausal Women*," Maturitas, 21(1), pp. 27-32.

Hoffmann, et al. (1998) "*Approaches To The Replacement Of Ethinylestradiol By Natural 17beta-Estradiol In Combined Oral Contraceptives*," Exp. Toxicol. Pathol., 50 (4-6) pp. 458-464.

Hoffman et al, (1999) "*Alternatives For The Replacement Of Ethinylestradiol By Natural 17beta-Estradiol In Dienogest-Containing Oral Contraceptives*"—Drugs of today, 35 (Suppl.C) pp. 105-113.

Insler, V., et al. (1972) "*The Cervical Score. A Simple Semiquantitative Method For Monitoring Of The Menstrual Cycle*," International Journal of Gynecology & Obstetrics, vol. 10, No. 6, pp. 223-228.

Jamin C. "*Contraception Macroprogestative: Avantages*" Contracept. Fertile. Sex. 1993, Fev; 21(2): 123-8, including an English translation.

Kivinen et Saure, "*Efficacy And Tolerability Of A Combined Oral Contraceptive Containing 17beta-Estradiol And Desogestrel*" 1996, The European Journal of Contraception and Reproductive Health care. p. 183.

Kuhl. "*Comparative Pharmacology Of Newer Progestogens*"—Drugs, Feb. 1996, 51(2), pp. 188-215.

Lindberg et al. (1989) "*A Comparison Between Effects Of Estradiol Valerate And Low Dose Ethinyl Estradiol On Haemostasis Parameters*" Thrombosis & Haemostasis, 61(1), pp. 65-69.

Mall-Haefeli, M., et al. (1991) "*Clinical Experience With Mercilon And Marvelon With Special Reference To Ovarian Function*," Geburtshilfe Frauerheilkd, 51, pp. 34-38.

Meade, T.W. (1988) "*Risks And Mechanisms Of Cardiovascular Events In Users Of Oral Contraceptives*" Am. J. Obstet. Gynecol. 158 (6 Pt 2) pp. 1646-1652.

Mizunuma et al., "*Prevention Of Postmenopausal Bone Loss With Minimal Uterine Bleeding Using Low Dose Continuous Estrogen/ Progestin Therapy: A 2-Year Prospective Study*" Maturitas 27, 1997, pp. 69-76.

Neumann "*Probleme der Dosisfindung: Sexualhormone*" Arzneim,- Forsch, Drug. Res, 27 (I), No. 2a (1977), pp. 296-318, including an English language abstract.

Neumann (1977) "*Pharmacology And Potential Use Of Cyproterone Acetate*," Horm. Metab Res., 9(1) pp. 1-13.

Nguyen -Pascal et al. "Nomegestrol Acetate May Enhance The Skeletal Effects Of Estradiol On Biochemical Markers Of Bone Turnover In Menopausal Women After 12-Week Treatment Period" Climacteric 2005; 8: 136-145.

O'Brien, P. (1999) "*Study Confirms Tendency Towards Lower Risk Of Myocardial Infarction With Second Generation Oral Contraceptives In UK*" BMJ., 319 (7218), pp. 1199.

Odlind, V., et al. (2002) "*Can Changes In Sex Hormone Binding Globulin Predict The Risk Of Venous Thromboembolisin With Combined Oral Contraceptive Pills?*" Acta Obstetricia et Gynecologi8ca Scandinavica, 81, pp. 482-490.

Oettel et al., "*The Preclinical And Clinical Profile Of Dienogest. A Short Overview*", Drugs of today, 1999, 35 (Suppl.C), pp. 3-12.

Organon "*Phase III program under way for oral contraceptive NOMAC/E2*" Internet Citation, Dec. 7, 2006 DailyDrugNews.com retrieved from the Internet: URL:http://integrity.prous.com.

"Organon Starts Phase III Development Of Unique Combined Oral Contraceptive" dated Jun. 11, 2006 and published on the website "Medical News today".

Paris, et al. (1987) "*Extinction Of Mineralocorticoid Effects In 19-Norprogesterone Derivatives: Structure-Activity Relationships*," The Journal of Pharmacology and Experimental Therapeutics, vol. 243, No. 1, pp. 288-291.

Paterson et al, "*Endometrial Disease After Treatment With Oestrogens And Progestogens In The Climacteric*" British medical journal, Mar. 22, 1980, 822-824.

Piegsa et al., "*Endometrial Status In Post-Menopausal Women On Long-Term Continuous Combined Hormone Replacement Therapy (Kliofem). A Comparative Study Of Endometrial Biopsy, Outpatient Hysteroscopy And Transvaginal Ultrasound*"—European Journal of Obstetrics & Gynecology and Reproductive biology (1997) 72, pp. 175-180.

Pons et al. "*L'acétate de nomégestrol dans le traitement des mastopathies bénignes Résultats d'un essai controlé*" Le Sein, 1996, Tome 6, No. 1: 3-7, including an English language abstract.

Rauch and Taubert, "*Continous Hormone Replaceament Therapy With Estradiol Valerate And Chlormadinone Acetate In Adjustable Dosages. A Preliminary Study*" 1993—Maturitas 17, pp. 123-127.

Recker et al., "*The Effect Of Low-Dose Continuous Estrogen And Progesterone Therapy With Calcium And Vitamin D on Bone In Elderly Women*"—Annals of Internal Medicine (Jun. 1999) vol. 130, No. 11, pp. 897-904.

Reubinoff et al., "*Effects Of Hormone Replacement Therapy On Weight, Body Composition, Fat Distribution, And Food Intake In Early Postmenopausal Women: A Prospective Study*"—Fertility & Sterility, (Nov. 1995), vol. 64, No. 5, pp. 963-968.

Sabra, A. & Bonnar, J. (1983) "*Hemostatic System Changes Induced By 50 μG And 30 μG Estrogen/Progestogen Oral Contraceptives. Modification Of Estrogen Effects By Levonorgestrel*" The Journal of Reproductive Medicine, 28, pp. 85-91.

Serup, et al. (1981) "*Effectivity And Acceptability Of Oral Contraceptives Containing Natural And Artificial Estrogens Investigation*," Acta Obstet. Gynecol. Scand., 60(2), pp. 203-206.

Suplemento anfa No. 1, may 1991, seccion II 57.

Spitzer (1997) "*The 1995 Pill Scare Revisted: Anatomy Of A Non-Epidemic*" Human Reproduction, vol. 12 (11) pp. 2347-2357.

Spona, J., et al. (1996) "*Shorter Pill Free Interval In Combined Oral Contraceptives Decreases Follicular Development,*" Contraception, 54, pp. 71-77.

Stadberg et al., "*17beta-Estradiol And Norethisterone Acetate On Low Doses As Continuous Combined Hormone Replacement Therapy*"—Maturitas 23, 1996, pp. 31-39.

Sullivan, H., et al. (1999) "*Effect Of 21-Day And 24-Day Oral Contraceptive Regimens Containing Gestodene (60 μG) And Ethinyl E2 (15 μG) On Ovarian Activity*", Fertility & Sterility, vol. 72, No. 1, pp. 115-120.

Thomas et al., "*Postmenopausal Hormone Replacement Therapy With Oestrogens And Nomegestrol Acetate. A Multicentric Study*" 7th International Congress on the Menopause, Stckholm, Jun. 20-24, 1993, abstr 372.

Thomas J. L., et al. "*Les Progestatifs—Effets Biologiques Et Implications Thérapeutiques3*" Revue française d'Endocrinologie, Nutition et Métabolisme, (1986), 27, No. 4-5, 389-403, including an English translation.

Timmer et al. "*Bioequivalence Assessment Of Three Different Estradiol Formulations In Postmenopausal Women In An Open, Randomized, Single-Dose, 3-Way Cross-Over Study*" Europ.J.Drug. Metab.& Pharmaco., 1999, vol. 24, No. 1, pp. 47-53.

Ulrich et al., "*Quality Of Life And Patient Preference For Sequential Versus Continuous Combined HRT: The UK Kliofem Multicenter Study Experience*"—International Journal of Gynecology & Obstetrics 59, suppl.1, (1997) pp. S11-S17.

Van Heusden A.M., Fauser BCJM (1999) "*Activity Of The Pituitary-Ovarian Axis In The Pill-Free Interval During Use Of Low-Dose Combined Oral Contraceptives*," Contraception, 59, pp. 237-243.

Von Schoultz, et al. (1989) "*Estrogen Therapy And Liver Function-Metabolic Effects Of Oral And Parenteral Administration*," Prostate, 14 (4), pp. 389-395.

Weil-Levy et al. "*Aspects Pharmacologiques Des Contraceptifs Oraux: Les Antigestagènes*" Contraception Fertility Sex Journal, vol. 8, No. 2 1980, including an English language abstract.

Wenzl et al (1993) "*Ovulation Inhibition With A Combined Oral Contraceptive Containing 1 Mg Micronized 17 Beta-Estradiol*," Fertility & Sterility, vol. 60, No. 4, pp. 616-619.

Whitehead et al., "*Effects Of Various Types And Dosages Of Progestogens On The Postmenopausal Endometrium*" The Journal of Reproductive Medicine, vol. 27, No. 8, Aug. 1982, pp. 539-548.

Williams et al., (Nov. 1998) "*Coadministration Of Nomegestrol Acetate Does Not Diminish The Beneficial Effects Of Estradiol On Coronary Artery Dilator Responses In Nonhuman Primates (Macaca fascicularis)*" Am. J. Obstet. Gynecol. vol. 179(5), pp. 1288-1294.

Wolfe and Huff, "*Effects Of Continuous Low-Dosage Hormonal Replacement Therapy On Lipoprotein Metabolism In Postmenopausal Women*"—Metabolism. vol. 44, N°3, (Mar. 1995), pp. 410-417.

Wolfe and Plunkett, "*Early Effects Of Continuous Low-Dosage Dl-Norgestrel Administered Alone Or With Estrogen*"—Maturitas 18, (1994), pp. 207-219.

World Health Organization Task Force on Oral Contraception (1980) "*A Randomized, Double-Blind Study Of Two Combined Oral Contraceptives Containing The Same Progestogen, But Different Estrogens*," Contraception, vol. 21, N°5, pp. 445-459.

Zartarian et al. (1998) "*Effets Sur La Qualités Des Cycles Et Les Bouffées De Chaleur Du Nomégestrol Acétate Administré Seul Ou Associé En Séquentiel Inversé Au 17 Bêta Estradiol Cutané Chez Des Femmes En Périménopause*" Contracept. Fertil. Sex. vol. 26(1), pp. 69-76, including an English language abstract.

Zartarian et al. (1998) "*Tolérance Biologique Et Clinique Du Nomégestrol Acégestrol Acétate, Administré Seul Puis Associé En Séquentiel Inversé Au 17 Bêta Estradiol Cutané, Chez Des Femmes À Risques Présentant Une Dyslipoprotéinémie De Type IIa*" Annales d'endicrinologie (Paris), 59, 411-416, including an English language abstract.

Zimmerman et al. (1999) "*Pharrnacokinetics Of Dienogest As A Single Drug Or In Combination With Estradiol Valerate Or Ethinylestradiol*," Drugs of today, 35, pp. 27-39.

\* cited by examiner

CONTRACEPTION METHOD

This application is a continuation-in-part of U.S. Ser. No. 10/753,073, filed Jan. 8, 2004, now abandoned, which was a continuation-in-part of (i) U.S. Ser. No. 09/284,147, filed Mar. 17, 1999, now U.S. Pat. No. 6,831,073, issued Dec. 14, 2004, §371 national stage of PCT International Application No. PCT/FR97/01792, filed Oct. 8, 1997, claiming priority of French Patent Application No. 96/12239, filed Oct. 8, 1996; and (ii) U.S. Ser. No. 09/423,108, filed Oct. 29, 1999, now U.S. Pat. No. 6,906,049, issued Jun. 14, 2005, claiming priority of PCT International Application No. PCT/FR99/02587, filed Oct. 25, 1999.

BRIEF SUMMARY OF THE INVENTION

The present invention relates to the field of therapeutic chemistry and more particularly to the field of hormonal pharmaceutical techniques.

DETAILED DESCRIPTION OF THE INVENTION

A more precise subject of the invention is new pharmaceutical compositions formed by an estroprogestative combination with a view to the correction of estrogenic deficiencies in natural or artificial menopauses or in order to stop ovulation of women during their period of ovarian activity.

In particular a subject of the invention is an estroprogestative combination, characterized in that it is constituted by unit doses containing the combination of a progestative and an estrogen, the two components being present simultaneously in each medicinal dose.

This combination is intended to be administered by oral route.

As is known, the life expectancy of women has passed in less than a century from 50 to 80 years, whilst the average age for the onset of the menopause has remained unchanged. Therefore, women spend a third of their life in a state of estrogenic deficiency which is the origin of the increase in risk of osteoporosis and cardiovascular illnesses.

Sequential replacement treatment for the menopause cures the climateric symptomology a id prevents osteoporosis and the onset of illnesses. It creates artificial cycles which are followed by a withdrawal bleeding. This therapeutic schema quite particularly suits women for whom the menopause is recent but it is not always well accepted in the long term, which in part explains the poorer observance of treatment (DRAPIER FAURE E.; Gynecologie. 1992, 43: 271-280).

In order to overcome this drawback, combined combinations have been perfected where the two components are taken simultaneously, the progestative having the effect of permanently opposing the proliferative action of the estrogen on the endometrium, by creating an atrophy of the endometrium and as a consequence, the absence of withdrawal bleeding (HARGROVE J. T., MAXSON W. S., WENTZ A. C., BURNETT L. S., Obstet Gynecol, 1989, 73: 606-612).

This "no periods" schema more particularly suits women for whom the menopause is already well in the past. It can be prescribed in courses of sequential combinations in order to improve the long-term observance of replacement hormone treatment for the menopause.

The dose of progestative to be used in a combined replacement treatment is in general deduced from that which is usually prescribed in sequential schemata. In the latter the dose chosen is that which gives over the long term less than 1% endometrial hyperplasia when the progestative is administered discontinuously, more than 10 days per cycle, in postmenopausal women under replacement estrogenotherapy (WHITEHEAD et al., J. reprod. Med, 1982, 27: 539-548, PATERSON et al, Br Med J, Mar. 22, 1980, 822-824).

In the combined treatment, these same progestatives were used at half the dose judged to be effective during a sequential treatment: this is the example of the micronized progesterone, didrogesterone (FOX H., BAAK J., VAN DE WEDER P., AL-AZZAWI E., PATERSON M., JOHNSON A., MICHELL G., BARLOW D., FRANCIS R., 7th International Congress on the Menopause, Stockholm, Jun. 20-24, 1993, abstr 119) and medroxyprogesterone acetate (BOCANERA R, BEN J., COFONE M., GUINLE I., MAILAND D., SOSA M., POUDES G., ROBERTI A., BISO T., EZPELETA D., PUCHE R., TOZZINI R., 7th International Congress on the Menopause, Stockholm, Jun. 20-24, 1993, abstr 40) which were used at doses of 100, 10 and 5 mg/day respectively, with encouraging results on the clinical and endometrial level.

Among the progestatives, nomegestrol acetate appeared to be one of the most effective. Nomegestrol acetate is a non-androgenic progestative derived from 19-nor progesterone, its use in sequential administration during the menopause at the dose of 5 mg/day, 12 days per cycle, in combination with different types of estrogens, allows endometrial hyperplasia to be prevented as shown by a multicentre study on 150 women for one year (THOMAS J. L., BERNARD A. M., DENIS C., 7th International Congress on the Menopause, Stockholm, Jun. 20-24, 1993, abstr 372).

The absence of hyperplasia was confirmed in a study where the nomegestrol acetate was administered at the same dose, 14 days per cycle, in women treated with percutaneous estradiol (BERNARD A. M. et al. Comparative evaluation of two percutaneous estradiol gels in combination with nomegestrol acetate in hormone replacement therapy. XIV World Congress of Gynecology and Obstetrics, FIGO, Montreal, Sep. 24-30, 1994).

The combined treatment is more often used in a continuous fashion, i.e. without interruption. However some people are in favour of using it in an intermittent fashion, for example 25 days per month (BLRKAUSER M. ET AL; Substitution hormonale: une indication bien posée et des schémas de traitement individuels sont déterminants pour le succès du traitement, Méd. et Hyg., 1995, 53: 1770-1773). The aim of the therapeutic interruption is to remove the inhibition exercised by the progestative on the synthesis of the estradiol and progesterone receptors and in this way to avoid the lowering of receptivity of the hormono-dependant tissues.

The progesterone used according to the present invention is nomegestrol acetate which is active by oral route.

The estrogen used is free or esterified estradiol, or conjugated equine estrogens which are presented according to a formulation which is active by oral route and in particular estradiol valerate.

Nomegestrol acetate and free or esterified estradiol or conjugated equine estrogens are administered in one of the forms which permit administration by oral route: gelatine capsules, capsules, pills, sachets of powder, tablets, coated tablets, sugar-coated tablets etc.

The present invention is characterized in that it is constituted by a new estroprogestative combination, which is active by oral route and administered in a combined manner. A subject of the present invention is also its use in the correction of estrogenic deficiencies, in the prevention of osteoporosis and cardiovascular illnesses in post-menopausal women, or in stopping ovulation in women during their period of ovarian activity.

The compositions according to the invention based on nomegestrol and free or esterified or equine conjugated estrogens are administered in a continuous fashion or intermittent fashion from 21 to 25 days per month.

According to a particular implementation of the invention the compositions contain a quantity of nomegestrol acetate ranging from 1.5 to 3.75 mg and a quantity of free or esterified estradiol or conjugated equine estrogens ranging from 0.5 to 3 mg. Preferably, the optimal formulations contain 2.5 mg of nomegestrol acetate combined with: either 1.5 mg of free estradiol or 2 mg of estradiol ester or 0.625 mg of conjugated equine estrogens, per daily dose.

This combined administration method can have several therapeutic indications. In post-menopausal women, the estroprogestative combination is intended to compensate for the functional disorders brought about by hypoestrogenism of the menopause, while maintaining an atrophy of the endometrium and avoiding in a majority of them the appearance of withdrawal bleeding.

In women during the period of ovarian activity, young or in the years preceding the menopause, the cyclic administration of the hormonal combination is capable of stopping ovulation and of exercising a contraceptive effect insofar as it has been proved that nomegestrol is capable of stopping the ovulation peak of LH and FSH, starting from 1.25 mg/day (BAZIN B. et al, Effect of nomegestrol acetate, a new 19-norprogesterone derivative on pituitary ovarian function in women. Br. 1. Obstet. Gynaecol., 1987, 94: 1199-1204). When the hormonal combination is given for a contraceptive purpose, the aim of nomegestrol acetate is to stop ovulation and for the estrogenic compound to compensate for hypoestrogenia and ensure a better control of the cycle.

A subject of the present invention is also a process for obtaining new pharmaceutical compositions.

The obtaining process according to the invention consists of mixing the active ingredients: nomegestrol acetate and free or esterified estradiol or conjugated equine estrogens with one or more pharmaceutically acceptable, non-toxic, inert excipients.

Among the excipients which can be mentioned are binding and solubilizing agents, compression agents, disintegration agents and slip agents.

This mixture can be subjected to direct compression or to several stages of compression in order to form tablets which, if desired, can have their surface protected by a film, by lacquering or coating. The production of tablets by direct compression allows a maximum reduction in the proportion of diluting agents, binding agents, disintegration agents and slip agents.

The production of gelatine capsules can be carried out by mixing the active ingredients with an inert diluent and a slip agent.

The tablets contain, in particular, mass diluting agents such as lactose, sorbitol for direct compression, marketed under the name NEOSORB 60, Palatinite which is a registered trademark for designating an equimolar mixture of the isomer of -D-glucopyranosido 1,6-mannitol and -D-glucopyranosido 1,6-glucitol crystallized with two molecules of water, mannitol, sorbitol or the mixture lactose/PVP sold under the name Ludipress.

The compression binding agents are in general microcrystalline celluloses such as those sold under the name AVICEL PH 101 or AVICEL PH 102.

The polyvinylpyrrolidone plays an important role and facilitates the agglomeration of the powders and the compressibility of the mass. To this end polyvinylpyrrolidones are used with a molecular weight comprised between 10000 and 30000 such as Povidone, Kollidon of a grade comprised between 12 and 30.

The mixture also contains slip or anti-electrostatic agents so that the powder does not agglomerate in the feed hoppers. In this respect, colloidal silicas can be mentioned which are sold under the name AEROSIL 100 or AEROSIL 200.

The mixture also contains disintegration agents which allow disintegration or crumbling which conforms to pharmaceutical standards. There can be mentioned as useful disintegration agents, polymers of cross-linked vinylpyrrolidones such as those sold under the names Polyplasdone or Polyclar AT, carboxymethylamidons such as those sold under the names Amigel or Explotab, cross-linked carboxymethylcelluloses or croscarmelloses such as the compound sold under the name AC-DI-SOL>.

In addition, the preparation contains lubrication agents which facilitate the compression and ejection of the tablet from the tablet compressing machine. There can be mentioned as lubrication agents, glycerol palmitostearate sold under the name Precirol, magnesium stearate, stearic acid or talc.

After compression the tablets can be coated in order to ensure their storage or to facilitate their deglutination.

The coating agents are either of cellulose origin such as cellulose phthalate (Sepifilm, Pharmacoat), or of polyvinyl origin of Sepifilm ECL type, or of saccharose origin such as the sugar for sugar-coating of Sepisperse DR, AS, AP OR K (coloured) type.

The tablets, whether coated or not, can in addition, be surface or bulk coloured, by plant or synthetic colouring agents (for example chinolin yellow lacquer or E 104).

The proportions of the different constituents vary according to the type of tablet to be produced.

The content of active ingredients can vary from 1.5 to 3.75 mg for nomegestrol acetate and from 0.5 to 3 mg for free or esterified estradiol or for conjugated equine estrogens. The dilution agents vary from 20 to 75% of the total mass, the slip agents from 0.1 to 2% of the total mass, the compression binding agents vary from 2 to 20%, the polyvinylpyrrolidone from 0.5 to 15%, the disintegration agents vary from 2 to 5.5% for the cross-linked polyvinylpyrrolidone or the carboxymethylamidon, from 2.0 to 3.0% for the croscarmellose.

The quantities of lubricating agents vary as function of the type of agents from 0.1 to 3.0%.

The compositions according to the invention are intended to be administered once per day. However, depending on the therapeutic requirements, administration can be split up (twice per day) or on the other hand, repeated (two tablets per day). The following examples illustrate the invention. They in no way limit it.

Example I

Tablets with 4 mg of Active Ingredient

| | | |
|---|---|---|
| Active ingredients: | estradiol | 1.5 mg |
| | nomegestrol acetate | 2.5 mg |
| Microcrystalline cellulose | | 22.4 mg |
| (marketed under the name AVICEL PH 102) | | |
| Lactose | | 60 mg |
| Polyvinylpyrrolidone | | 8.4 mg |
| Colloidal silica | | 1.2 mg |
| Glycerol palmitostearate | | 3.6 mg |
| Colouring agent E.104 | | 0.4 mg | for a tablet completed at an average weight of 100 mg.

Example II

Study of the Clinical Tolerance During Two Continuous Combined Schemata of Hormone Replacement Therapy for the Menopause The pilot study is carried out over 24 weeks on two parallel groups subjected to treatments A and C:

Treatment A
  Nomegestrol acetate 2.5 mg/day every day+percutaneous 17β-estradiol 1.5 mg/day every day.
  The nomegestrol acetate is administered in the form of tablets and the percutaneous 17β-estradiol in the form of a gel.

Treatment C
  Nomegestrol acetate 2.5 mg/day every day+estradiol valerate 2 mg/day every day.
  The estradiol valerate is administered in the form of tablets.

The pilot study is intended to evaluate the endometrial clinical tolerance during the use of the two hormone replacement therapy schemata for the menopause so called "without periods" combining in a continuous combined fashion treatment A or C. The endometrial clinical tolerance is evaluated from the presence or not of occurrences of vagina bleeding, their intensity, their frequency, from data acquired from endovaginal echographical examination etc.

Also, another aim of this study is to assess the general clinical tolerance (weight, blood pressure, mammary symptoms), biological tolerance (Formule Numeration Sanguine (blood count), glycemia, cholesterol . . . ), as well as the observance of treatment.

The selection of subjects is carried out as a function of "inclusion" criteria. These criteria are to do:

with the menopause:

women over 50 years old are included who have had a natural menopause expressed clinically by an amenorrhea greater than 12 months and less than 10 years, the women having had a natural menopause confirmed biologically by quantitative analysis of FSH (Follicle stimulating hormone) and estradiol (i.e. plasmatic FSH$\geq$20 IU/I, plasmatic $E_2 \leq 0.11$ nmol/l).

with women:

women who have not had hysterectomies are included, whose Quetelet's index (weight in kg/(height in m)$^2$) is $\leq$27, having had regular cycles before the menopause, having never received hormone replacement therapy for the menopause or having had a clinically well tolerated hormone replacement therapy (absence of abnormal bleeding), interrupted for more than 6 weeks, presenting an endometrial thickness measured by endovaginal echography $\leq$5 mm, accepting the idea of hormone replacement therapy for the menopause, who would like a hormone therapy without periods, justifying an estroprogestative hormone therapy for at least 6 months, cooperative: accepting to conform to the requirements of the study, whose psychic and intellectual profile would allow one to suppose a good observance of the treatment, having a mammograph dating from less than a year from the date of inclusion.

At the start of treatment the patients undergo an inclusion consultation ($C_1$) the purpose of which is to verify that the inclusion criteria have been respected, that the endovaginal echograph is normal and to obtain the written consent of the patient as regards participation.

The intermediate consultation ($C_2$) takes place between the 9th and 11th week of treatment, the purpose of which is to verify mammary and endometrial clinical tolerance is good as regards the treatment.

Lastly, a final consultation ($C_3$) takes place during the 24th week of treatment.

The patients who wish to continue the study can receive, for 24 additional weeks, the estroprogestative treatment received during the study according to the same therapeutic schema. The extension of the study thus allows a complete monitoring of the study over 48 weeks.

Analysis of the Study

Results I

The attached Tables I and II, reveal a difference in terms of the amenorrhea results (i.e. no bleeding from 0 to 24 weeks) and of mammary and/or endometrial tolerance as a function of the estrogen.

TABLE I

Treatment A
Nomegestrol acetate + percutaneous 17β-estradiol

| Elapse since menopause ameno/month | Presence of HRT previously | Start of treatment | Duration of treatment weeks | Endometrial thickness before/after mm | COMMENTS |
| --- | --- | --- | --- | --- | --- |
| 72 | no | 17 Oct. 1994 | 24<br>24 ext | 2/2 | Amenorrhea<br>endometrial thickness after 48 weeks of treatment = 2 mm |
| 82 | no | 04 Nov. 1994 | 24 extension | 3/3 | amenorrhea |
| 26 | yes<br>well tolerated | 09 Jan. 1995 | 24 extension | 3/3 | amenorrhea |
| 108 | no | 16 Jan. 1995 | 24 extension | 1/4 | amenorrhea |
| 48 | no | 13 Feb. 1995 | 24 | 3/2 | 1 episode of bleeding at 42 days (a few drops) between the 1$^{st}$ and 6$^{th}$ weeks; breast tension and pain of minimal intensity from the 1st to the 22nd week (7 days/week)<br>Extension not effected: did not pick up the treatment kit owing to holidays; following the same treatment outside protocol |
| 24 | no | 10 Mar. 1995 | 24 extension | 2/5 | Amenorrhea; breast tension and pain of slight intensity from the 6th to the 12th week (7 days/week) |

TABLE I-continued

Treatment A
Nomegestrol acetate + percutaneous 17β-estradiol

| Elapse since menopause ameno/month | Presence of HRT previously | Start of treatment | Duration of treatment weeks | Endometrial thickness before/after mm | COMMENTS |
|---|---|---|---|---|---|
| 55 | yes well tolerated | 20 Mar. 1995 | 24 extension | 4/8 | amenorrhea |
| 27 | yes well tolerated | 08 May 1995 | 24 | 3/5 | Amenorrhea Extension not effected: did not pick up the treatment kit owing to holidays; same treatment outside protocol |
| 90 | yes well tolerated | 10 Apr. 1995 | 24 extension | 4/4 | amenorrhea |
| 13 | yes well tolerated | 03 Jul. 1995 | 24 extension | 1 pending | amenorrhea |
| 99 | yes well tolerated | 24 Apr. 1995 | 24 extension | 1/4 | amenorrhea |
| 21 | yes well tolerated | 26 Jun. 1995 | 24 extension | 4 pending | amenorrhea |
| 96 | ? | 29 May 1995 | 24 extension | 2 pending | amenorrhea |
| 65 | yes well tolerated | 10 May 1995 | 24 extension | 1/3 | amenorrhea; 10 episodes (4 days/week) of breast pains of minimal intensity |
| 13 | no | 12 Jun. 1995 | Stopped at 6 | 3 not measured | continuous slight bleeding from the 5th week until treatment stopped |
| 38 | yes well tolerated | 10 Jul. 1995 | 24 extension | 2 pending | amenorrhea |

EXTENSION = 24 additional weeks of treatment
HRT = hormone replacement therapy

Conclusion

Of the 16 patients treated:
1 left the study, i.e. 6%

15 finished the study after 24 weeks, i.e. 94%
13 extensions of treatment (24 additional weeks) 81%

The two extensions which did not take place when due to reasons which were independent of the treatment, the patients continued the same treatment outside the treatment protocol.

TABLE II

Treatment C
Nomegestrol acetate + estradiol valerate per os

| Elapse since menopause ameno/month | Presence of HRT previously | Start of treatment | Duration of Treatment weeks | Endometrial Thickness before/after mm | COMMENTS |
|---|---|---|---|---|---|
| 72 | no | 21 Nov. 1994 | stopped at 8 | 4/* | amenorrhea, breast tension and pain of slight intensity from the 2nd week to the 8th week; STOPPED owing to high abdominopelvic tension due to increased size of a sub-serous fibroma: echo before treatment = 37 mm; echo after 8 weeks of treatment = 75 mm |
| 46 | yes well tolerated | 28 Nov. 1994 | 24 extension | 3/6 | 1 episode of bleeding of 31 days between the $5^{th}$ and the $9^{th}$ week (a few drops) |
| 31 | yes well tolerated | 28 Nov. 1994 | stopped at 10 | 2 not measured | amenorrhea, STOPPED for insomnia, nervousness and pain in lower limbs |
| 60 | yes well tolerated | 30 Jan. 1995 | 24 extension | 4/2 | amenorrhea, breast tension and pain of slight intensity from $2^{nd}$ week of treatment until the $19^{th}$ week |
| 121 | yes well tolerated | 06 Feb. 1995 | stopped at 9 | 3 not measured | 1 episode of bleeding of 16 days of low intensity from the 6th week; breast tension of minimal intensity from the 2nd week to the $8^{th}$ week; STOPPED owing to headaches, night sweats and a blood pressure of 17/10 |
| 36 | yes well tolerated | 06 Feb. 1995 | 24 | 4* | amenorrhea, 23 episodes of breast tension of high intensity of 7 days/week; extension impossible as estrogen dose reduced due to breast tension |
| 47 | yes well tolerated | 27 Feb. 1995 | 24 extension | 2/2 | amenorrhea; 6 episodes of breast tension and pain of slight intensity (2 days/week) |
| 62 | no | 13 Mar. 1995 | 24 extension | 1/4 | amenorrhea |
| 74 | yes well tolerated | 20 Mar. 1995 | 24 extension | 4/6 | amenorrhea |
| 110 | yes well tolerated | 08 May 1995 | stopped at 18 | 2 not measured | amenorrhea until 12 weeks then 1 episode of bleeding of 41 days until treatment stopped |
| 16 | yes well tolerated | 22 May 1995 | 24 extension | 1 pending | amenorrhea |

TABLE II-continued

Treatment C
Nomegestrol acetate + estradiol valerate per os

| Elapse since menopause ameno/month | Presence of HRT previously | Start of treatment | Duration of Treatment weeks | Endometrial Thickness before/after mm | COMMENTS |
|---|---|---|---|---|---|
| 60 | yes well tolerated | 12 Jun. 1995 | stopped at 16 | 2/3 | 4 episodes of bleeding of low intensity (6 days/week) 5 episodes of breast pain of medium intensity (6 days/week); STOPPED owing to mastitis and a breast abscess |
| 11 | no | 19 Jun. 1995 | 24 extension | 2 pending | 1 episode of bleeding 12 days (a few drops) |
| 38 | yes well tolerated | 03 Jul. 1995 | stopped at 4 | 5 not measured | 1 episode of bleeding of 11 days until treatment stopped of low intensity |

*= not measured at the control echo

Conclusion

Of the 14 patients treated
6 left the study i.e. 43%
8 finished the study after 24 weeks, i.e. 57%
7 extensions of treatment (24 additional weeks), i.e. 50%
% of amenorrhea (i.e. no occurrence of bleeding for 24 weeks)=43%

Results II

A—Observance

While no significant difference exists between the two groups A and C, a lower number of days when treatment lapsed over all the 24 weeks of the study was observed with treatment A.

B—Endometrial Clinical Tolerance

The most significant absolute percentage of amenorrhea is found in group A, the difference being significant in phase II (13th to 24th week of treatment) As has been described in the literature, the percentage of amenorrhea increases with time; therefore, for group C, it is 35.3% during the first 12 weeks of treatment, and 46.1% during the last 12 weeks.

The attached tables III, IV and V illustrate the results obtained.

Amenorrhea

Analysis Regarding Treatment

TABLE III

Phase I/weeks 1 to 12

|  | TOTAL | | GROUP A | | GROUP C | | |
|---|---|---|---|---|---|---|---|
|  | N | % | N | % | N | % | P |
| Amenorrhea | | | | | | | |
| yes | 19 | 37.2% | 9 | 50% | 6 | 35.3% | |
| no | 32 | 62.7% | 9 | 50% | 11 | 64.7% | 0.316 |
| Spotting | | | | | | | |
| yes | 32 | 62.7% | 9 | 50% | 11 | 64.7% | |
| no | 19 | 37.2% | 9 | 50% | 6 | 35.3% | 0.316 |

|  | TOTAL | | GROUP A | | GROUP C | | |
|---|---|---|---|---|---|---|---|
|  | N | avg ± week (min:max) | N | avg ± week (min:max) | N | avg ± week (min:max) | P |
| Total duration of bleeding (days) | 51 | 9.1 ± 2.1 0:70 | 18 | 9.1 ± 4.5 0:70 | 17 | 8.9 ± 2.7 0:31 | 0.412 |
| Average intensity | 51 | 0.8 ± 0.1 0:2 | 18 | 0.7 ± 0.2 0:2 | 17 | 0.9 ± 0.2 0:2.5 | 0.446 |
| Number of weeks of bleeding | 51 | 2.1 ± 0.4 0:10 | 18 | 1.8 ± 0.7 0:10 | 17 | 2.1 ± 0.5 0:7 | 0.552 |
| Total number of episodes | 51 | 1.2 ± 0.2 0:6 | 18 | 1 ± 0.3 0:4 | 17 | 1.2 ± 0.4 0:6 | 0.434 |

None of the patients suffered from metrorrhagias during phase I

TABLE IV

Phase II/weeks 13 to 24

| | TOTAL | | GROUP A | | GROUP C | | |
|---|---|---|---|---|---|---|---|
| | N | % | N | % | N | % | P |
| Amenorrhea | | | | | | | |
| yes | 20 | 42.5% | 12 | 66.7% | 6 | 46.1% | |
| no | 27 | 57.4% | 6 | 33.3% | 7 | 53.8% | 0.006 |
| Spotting | | | | | | | |
| yes | 27 | 57.4% | 6 | 33.3% | 7 | 53.8% | |
| no | 20 | 42.5% | 12 | 66.7% | 6 | 46.1% | 0.006 |

| | TOTAL | | GROUP A | | GROUP C | | |
|---|---|---|---|---|---|---|---|
| | N | avg ± week (min:max) | N | avg ± week (min:max) | N | avg ± week (min:max) | P |
| Total duration of bleeding (days) | 47 | 13.9 ± 3.1 0:75 | 18 | 6.2 ± 3.3 0:42 | 13 | 18.5 ± 7.7 0:75 | 0.013 |
| Average intensity | 47 | 0.9 ± 0.1 0:2 | 18 | 0.6 ± 0.2 0:2.33 | 13 | 1.0 ± 0.3 0:2 | 0.055 |
| Number of weeks of bleeding | 47 | 2.9 ± 0.6 0:12 | 18 | 1.3 ± 0.6 0:9 | 13 | 3.3 ± 1.2 0:11 | 0.007 |
| Total number of episodes | 47 | 1.3 ± 0.3 0:7 | 18 | 0.6 ± 0.3 0:6 | 13 | 1.1 ± 0.5 0:7 | 0.002 |

None of the patients suffered from metrorrhagias during phase II

TABLE V

| Δ % | TOTAL | | GROUP A | | GROUP C | | |
|---|---|---|---|---|---|---|---|
| Between C1 And C3 | N | avg ± week (min:max) | N | avg ± week (min:max) | N | avg ± week (min:max) | P |
| A.L.A.T. | 43 | −23.1% ± 5.2% −88.2%:85.7% | 17 | −19.0% ± 3.8% −50%:7.1% | 11 | −31.2% ± 13.2% −88.2%:29.4% | 0.936 |
| F.S.H. | 45 | −74.1% ± 4.9% −98.4%:69.2% | 18 | −72.2% ± 5.5% −98%:24.8% | 12 | −78.2% ± 9.6% −98.4%:22.8% | 0.405 |
| Estradiol (pg/ml) | 40 | 432% ± 68.5% −54%:1640% | 15 | 567% ± 118.7% −16%:1320% | 10 | 609% ± 163.6% −54.3%:1640% | 0.036 |

A.L.A.T. = Alanine Aminotransferase Transaminase
F.S.H.—Follide Stimulating Hormone The relative variation in estradiol level is quite important in the two groups (Δ%=567% in group A and 609% in group C), p=0.04

Table VI illustrates another study which was carried out. In this other study, it is interesting to note that with nomegestrol acetate, the percentage of patients with absolute amenorrhea (including all forms of estrogenotherapy) is greater from the 3rd month of treatment: 42.5% against 33.3%. In the treatment mentioned above, one must wait until the 12th month of treatment to obtain this percentage of 42% of patients with amenorrhea which was obtained here from 3 months, whilst the populations are comparable in terms of age, weight and length of time since the menopause. In addition, there exists in the previous study, an estrogen effect which is not found in this other study. On the other hand, this study reveals a dosage effect of progestative during the last 9 months of treatment (the lower the dose of progestative the better the cycle is controlled).

Finally, it is interesting to note that no correlation exists between the existence of an amenorrhea at 6 months and the endometrial thickness measured by endovaginal echography; this thickness varying by +1.6 mm on average over 6 months in the 2 treatment groups.

TABLE VI

Characteristics of the patients

| | TOTAL | | GROUP A | | GROUP C | | |
|---|---|---|---|---|---|---|---|
| | N | avg ± week (min:max) | N | avg ± week (min:max) | N | avg ± week (min:max) | P |
| Age | 54 | 54.9 ± 0.6 45:64 | 19 | 53.9 ± 0.8 48:60 | 17 | 54.9 ± 1.1 45:63 | 0.321 |

TABLE VI-continued

Characteristics of the patients

| | TOTAL | | GROUP A | | GROUP C | | |
|---|---|---|---|---|---|---|---|
| Age of amenorrhea (months) | 54 | 56.1 ± 5.0  7:134 | 19 | 48.5 ± 7.7  12:108 | 17 | 50.7 ± 7.7  11:121 | 0.309 |
| Weight (kg) | 54 | 60 ± 1.1  42:85 | 19 | 61.6 ± 1.2  51:70 | 17 | 60.8 ± 2.2  12:76 | 0.149 |
| Height | 54 | 1.61 ± 0.01  1.47:1.75 | 19 | 1.62 ± 0.01  1.57:1.75 | 17 | 1.61 ± 0.02  1.47:1.75 | 0.449 |
| Quetelet's index (kg/m$^2$) | 54 | 23.1 ± 0.4  17.1:31.2 | 19 | 23.3 ± 0.4  19.7:25.6 | 17 | 23.5 ± 0.7  17.5:28.7 | 0.3182 |
| SBP (mmHg) | 54 | 123.9 ± 1.5  100:140 | 19 | 127.9 ± 2.5  110:140 | 17 | 121.2 ± 2.5  110:140 | 0.136 |
| DBP (mmHg) | 54 | 74.6 ± 1.2  60:90 | 19 | 76.8 ± 2  60:90 | 17 | 73.5 ± 2.3  60:90 | 0.386 |

| H.R.T. | TOTAL | | GROUP A | | GROUP C | | |
|---|---|---|---|---|---|---|---|
| Previous HRT's | N | % | N | % | N | % | P |
| yes | 17 | 31.5% | 9 | 47.4% | 14 | 82.3% | |
| no | 37 | 68.5% | 10 | 52.6% | 8 | 17.7% | 0.046 |

HRT = Hormone Replacement Therapy
SBP = Systolic Blood Pressure
DBP = Diasystolic Blood Pressure

What is claimed is:

1. A method of achieving contraception in a woman comprising the cyclic oral administration to said woman of an estroprogestative composition comprising 1.5 mg to 3.75 mg of nomegestrol acetate and 0.5 mg to 3 mg of a free or esterified estradiol or a conjugated equine estrogen, in an intermittent fashion from 21 to 25 days per month.

2. The method according to claim 1, in which the estroprogestative composition comprises an estradiol ester.

3. The method according to claim 2, in which the estradiol ester is estradiol valerate.

4. The method according to claim 1, in which the estroprogestative composition comprises 2.5 mg of nomegestrol acetate.

5. The method according to claim 1, in which the estroprogestative composition comprises 2.5 mg of nomegestrol acetate and 2 mg of estradiol ester.

6. The method according to claim 1, in which the estroprogestative composition comprises 2.5 mg of nomegestrol acetate and 0.625 mg of equine conjugated estrogens.

7. A method of achieving contraception in a woman comprising administering orally to said woman in a continuous fashion an estroprogestative composition comprising 1.5 to 3.75 mg of nomegestrol acetate and 0.5 mg to 3 mg of a free or esterified estradiol or a conjugated equine estrogen.

8. The method according to claim 7, in which the estroprogestative composition comprises an estradiol ester.

9. Method according to claim 8, in which the estradiol ester is estradiol valerate.

10. The method according to claim 7, in which the estroprogestative composition comprises 2.5 mg of nomegestrol acetate.

11. The method according to claim 7, in which the estroprogestative composition comprises 2.5 mg of nomegestrol acetate and 1.5 mg of free estradiol.

12. The method according to claim 7, in which the composition comprises 2.5 mg of nomegestrol acetate and 2 mg of estradiol ester.

13. The method according to claim 7, in which the estroprogestative composition comprises 2.5 mg of nomegestrol acetate and 0.625 mg of equine conjugated estrogens.

14. A method of achieving contraception in a woman comprising the cyclic oral administration to said woman of an estroprogestative composition comprising 1.5 mg to 3.75 mg of nomegestrol acetate and 0.5 mg to 3 mg of a free or esterified estradiol in an intermittent fashion from 21 to 25 days per month.

15. The method according to claim 14, in which the estroprogestative composition comprises 2.5 mg of nomegestrol acetate and 1.5 mg of free estradiol.

* * * * *

UNITED STATES PATENT AND TRADEMARK OFFICE
CERTIFICATE OF CORRECTION

PATENT NO.        : 7,749,987 B2                                    Page 1 of 1
APPLICATION NO.   : 11/649672
DATED             : July 6, 2010
INVENTOR(S)       : Jacques Paris et al.

It is certified that error appears in the above-identified patent and that said Letters Patent is hereby corrected as shown below:

On the Title Page, Item "(73) Assignee: Laboratoire Theramek (MC)" should read -- (73) Assignee: Laboratoire Theramex (MC) --

In claim 12, column 14, lines 35-36: "the composition" should read -- the estroprogestative composition --

Signed and Sealed this

Twenty-first Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,749,987 B2  Page 1 of 1
APPLICATION NO. : 11/649672
DATED : July 6, 2010
INVENTOR(S) : Jacques Paris et al.

It is certified that error appears in the above-identified patent and that said Letters Patent is hereby corrected as shown below:

On the title page, Item [63] should read as follows:

--Continuation-in-part of application U.S. Serial No. 10/753,073, filed January 8, 2004, now abandoned, which was a continuation-in-part of: (i) U.S. Serial No. 09/284,147, filed March 17, 1999, now U.S. Patent No. 6,831,073, issued December 14, 2004, a § 371 national stage of PCT International Application No. PCT/FR97/01792, filed October 8, 1997, claiming priority of French Patent Application No. 96/12239, filed October 8, 1996, and (ii) U.S. Serial No. 09/423,108, filed October 29, 1999, now U.S. Patent No. 6,906,049, issued June 14, 2005, claiming priority of PCT International Application No. PCT/FR99/02587, filed October 25, 1999.--;

In the Specification

In column 1, line 7, "2004, § 371 national stage" should read --2004, a § 371 national stage--;

In column 1, line 42, "a id" should read --and--.

Signed and Sealed this
Twentieth Day of August, 2013

Teresa Stanek Rea
*Acting Director of the United States Patent and Trademark Office*